United States Patent
Badbada et al.

(10) Patent No.: US 11,464,952 B2
(45) Date of Patent: Oct. 11, 2022

(54) TREATMENT FOR HYDROCEPHALUS

(71) Applicant: MicroVention, Inc., Aliso Viejo, CA (US)

(72) Inventors: Wenmar Badbada, Orange, CA (US); Nga Ting Wong, Santa Ana, CA (US); Heath Bowman, Trabuco Canyon, CA (US); Matt Biggers, Greensboro, NC (US); Joseph Rye, Oceanside, CA (US); Jared Shimizu, Irvine, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 230 days.

(21) Appl. No.: 16/403,360

(22) Filed: May 3, 2019

(65) Prior Publication Data

US 2019/0336735 A1  Nov. 7, 2019

Related U.S. Application Data

(60) Provisional application No. 62/666,636, filed on May 3, 2018.

(51) Int. Cl.
*A61M 27/00* (2006.01)
*A61L 29/08* (2006.01)
(Continued)

(52) U.S. Cl.
CPC ......... *A61M 27/006* (2013.01); *A61L 29/085* (2013.01); *A61L 29/148* (2013.01); *A61M 25/007* (2013.01); *A61M 25/0074* (2013.01); *A61M 2025/0019* (2013.01); *A61M 2205/0238* (2013.01); *A61M 2205/3341* (2013.01);
(Continued)

(58) Field of Classification Search
CPC .............. A61M 27/006; A61M 25/007; A61M 2025/0019; A61M 2205/3341; A61M 2210/0693; A61M 2210/125; A61M 25/0074; A61M 2205/0238; A61L 29/085; A61L 29/148; A61L 31/10
See application file for complete search history.

(56) References Cited

U.S. PATENT DOCUMENTS

| 5,385,541 A | 1/1995 | Kirsch et al. |
| 9,113,857 B2 * | 8/2015 | Sethi ................. A61B 10/0266 |

(Continued)

FOREIGN PATENT DOCUMENTS

| CN | 1879555 A | 12/2006 |
| CN | 101435430 A | 5/2009 |

(Continued)

OTHER PUBLICATIONS

WIPO, U.S. International Search Authority, International Search Report and Written Opinion dated Jul. 12, 2019 in International Patent Application No. PCT/US19/30726, 12 pages.

(Continued)

*Primary Examiner* — Tatyana Zalukaeva
*Assistant Examiner* — Hans Kaliher
(74) *Attorney, Agent, or Firm* — Inskeep IP Group, Inc.

(57) ABSTRACT

A shunt system used to treat excess cerebrospinal fluid (CSF) accumulation is described. In some embodiments, the system utilizes various mechanical, electrical, or electromechanical concepts designed to either clean a portion of the shunt system, or customize CSF drainage.

20 Claims, 10 Drawing Sheets

(51) Int. Cl.
*A61L 29/14* (2006.01)
*A61M 25/00* (2006.01)

(52) U.S. Cl.
CPC ............... *A61M 2210/0693* (2013.01); *A61M 2210/125* (2013.01)

(56) References Cited

U.S. PATENT DOCUMENTS

| | | | |
|---|---|---|---|
| 10,010,392 B1* | 7/2018 | Zukowski | A61M 25/0017 |
| 2004/0236309 A1 | 11/2004 | Yang | |
| 2005/0085763 A1 | 4/2005 | Ginggen et al. | |
| 2006/0062824 A1 | 3/2006 | Pacetti et al. | |
| 2006/0216326 A1 | 9/2006 | Pacetti | |
| 2008/0167712 A1 | 7/2008 | DesNoyer et al. | |
| 2010/0228179 A1 | 9/2010 | Thomas et al. | |
| 2013/0102951 A1 | 4/2013 | Swoboda et al. | |
| 2013/0158464 A1* | 6/2013 | Samoocha | B08B 9/027 604/8 |
| 2013/0310767 A1* | 11/2013 | Solar | A61M 39/22 604/247 |
| 2014/0150782 A1* | 6/2014 | Vazales | A61M 16/04 128/202.16 |
| 2015/0328374 A1 | 11/2015 | Mihov et al. | |
| 2016/0287848 A1 | 10/2016 | Samoocha et al. | |
| 2020/0353231 A1* | 11/2020 | Sharon | A61M 25/007 |

FOREIGN PATENT DOCUMENTS

| | | | |
|---|---|---|---|
| CN | 102319474 A | 1/2012 | |
| CN | 202191577 U | 4/2012 | |
| CN | 103037919 A | 4/2013 | |
| CN | 104014069 A | 9/2014 | |
| CN | 205411171 U | 8/2016 | |
| EP | 3315162 A1 | 10/2017 | |
| JP | 2008534062 A | 8/2008 | |
| JP | 2016508752 A | 3/2016 | |
| WO | WO2006102418 A2 | 9/2006 | |
| WO | WO2014096339 A1 | 6/2014 | |

OTHER PUBLICATIONS

European Patent Office, Supplementary Extended European Search Report dated May 18, 2021 in European Patent Application No. 19795875.4, 28 pages.

Japanese Patent Office, Office Action dated May 11, 2021 with English translation in Japanese Patent Application No. 2020-561700, 8 pages.

Chinese Patent Office, Notification to Make Divisional Application dated May 24, 2021 with English translation in China Patent Application No. 201980045046.6, 4 pages.

Thomson Scientific, London, GB; Database WPI, Week 201214, AN 2012-B63469, XP002802904, & CN 102 319 474 A (Kong J) Jan. 18, 2012 (Jan. 18, 2012), 2 pages.

Thomson Scientific, London, GB; Database WPI, Week 201232, AN 2012-E90290; XP002802905, & CN 202 191 577 U (Kong J) Apr. 18, 2012 (Apr. 18, 2012), 2 pages.

China Patent Office, Office Action dated Sep. 30, 2021 with English translation in Chinese Patent Application No. 201980045046.6, 12 pages.

European Patent Office, Supplementary Extended European Search Report dated Aug. 18, 2021 in European Patent Application No. 19795875.4, 17 pages.

Thomson Scientific, London, GB; Database WPI, Week 201214, AN 2012-B63469, XP002802904, & CN 102 319 474 A (Kong J) Jan. 18, 2012 (Jan. 18, 2012), with Annex, 5 pages.

Thomson Scientific, London, GB; Database WPI, Week 201232, AN 2012-E90290; XP002802905, & CN 202 191 577 U (Kong J) Apr. 18, 2012 (Apr. 18, 2012), with Annex, 5 pages.

* cited by examiner

TREATMENT FOR HYDROCEPHALUS

RELATED APPLICATIONS

This application claims priority to U.S. Provisional Application Ser. No. 62/666,636 filed May 3, 2018 entitled Treatment for Hydrocephalus and Ventriculoperitoneal Shunt, which is hereby incorporated herein by reference in its entirety.

BACKGROUND OF THE INVENTION

Cerebrospinal Fluid (CSF) is a fluid found in the brain and spinal cord. CSF is produced in the choroid plexus of the ventricles of the brain and serves several purposes—including acting as a cushion for the brain, acting as a mechanism for delivering nutrients from and removing waste from the brain, and regulating changes in pressure within the brain. When CSF production exceeds its absorption, the pressure from CSF rises which can lead to an abundance of CSF—this in turn can result in hydrocephalus, which is swelling of the brain due to buildup of CSF. Hydrocephalus can cause balance and vision issues, increased head size, bleeding in the brain, cerebral edema, impaired brain function, brain herniation, as well as other issues.

One method to treat hydrocephalus is known as shunting, which involves routing the CSF from the brain to another region of the body, such as the abdomen, lung, or heart. One popular routing area is the peritoneal cavity in the abdomen; routing from the brain ventricles to the peritoneal cavity is known as Ventriculoperitoneal (VP) shunting. The shunt system utilizes a ventricular catheter in the brain to collect and route the CSF, a second drainage catheter to redirect the CSF to another region of the body (e.g., the peritoneal cavity), and a valve in between to regulate flow of CSF from the brain to the drainage region.

There are several complications associated with shunting. One is that the CSF can clog the catheter over time, this problem is more pronounced in the ventricular catheter since it has more exposure to CSF. This clogging can dilute the effectiveness of shunting and necessitate replacement over time. Next, it can be difficult to calibrate the valve correctly to drain the correct amount of CSF from the brain—draining too much CSF will decrease the available CSF while draining too little will not address the issue of hydrocephalus. Furthermore, the typical mechanical valves which regulate CSF flow to the drainage system have high failure rates for a variety of reasons.

There is a need for a shunting device and system that addresses these issues.

SUMMARY OF THE INVENTION

The present invention relates to devices, systems, and methods designed to address issues with the shunting procedure.

In some embodiments, a shunting system includes a cleaning mechanism designed to clean residue from CSF in the ventricular catheter of a broader shunting system. In one embodiment, the cleaning mechanism includes a spring plunging element used to clean slits that allow CSF passage. In one embodiment, the cleaning mechanism includes a cleaning piston element used to clean slits allowing CSF passage. In one embodiment, the cleaning mechanism includes a rotational element used to clean slits allowing CSF passage.

In one embodiment, a ventricular catheter used in a CSF draining shunt system includes slits to facilitate CSF drainage and biodegradable or bioresorbable material along one or more of these slits.

In one embodiment, a locking mechanism facilitating secure fitting between a catheter tubing and a shunt valve element is described.

In one embodiment, a mechanical valve utilizing a weighted or thinned disc portion is described. The mechanical valve regulates CSF flow within a valve housing, between a CSF inlet and CSF outlet.

In one embodiment, a hydrogel is utilized to seal a hole opening used to gain vascular access during the CSF shunting procedure.

In one embodiment, an electrical system used to monitor and/or communicate patient data associated with a CSF shunt system is described.

In one embodiment, the shunt system includes a mechanical, electromechanical, and/or an electrical mechanism to selectively regulate CSF flow.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
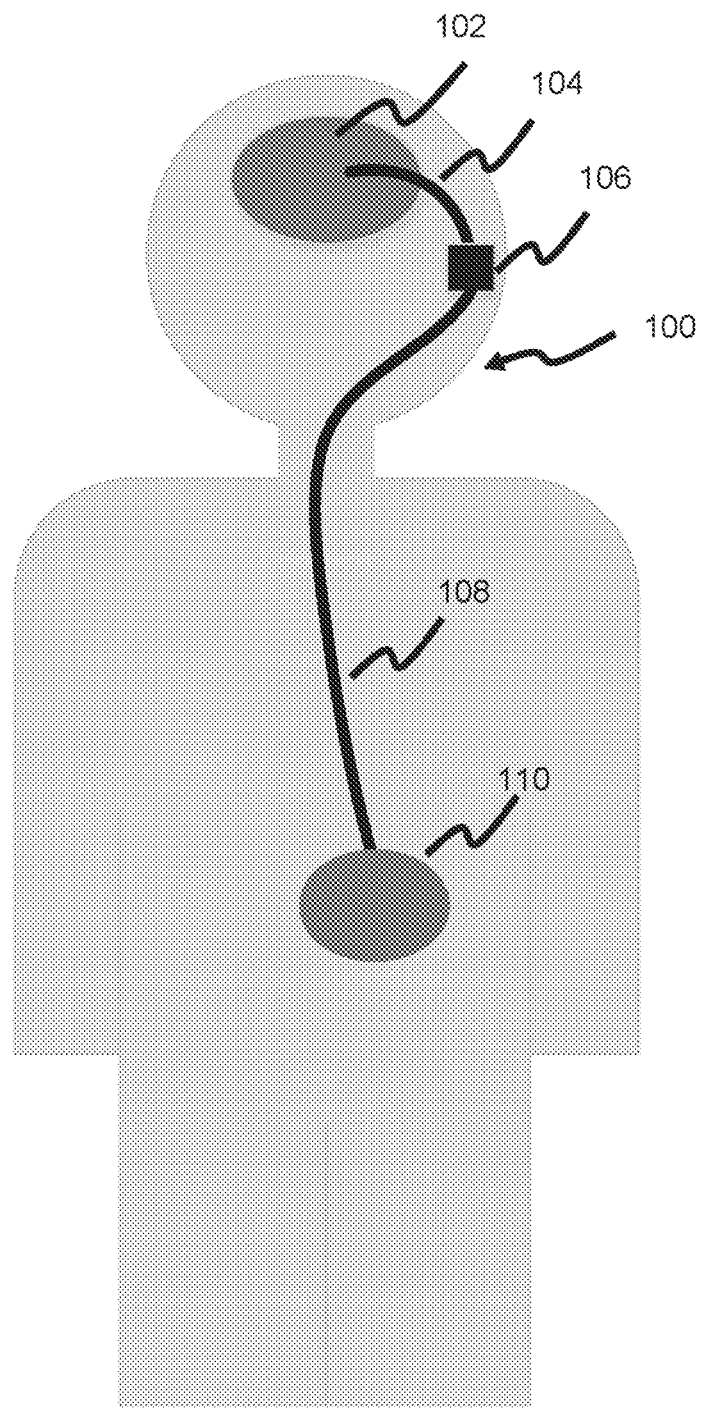
FIG. 1 illustrates a shunt system.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Excessive CSF production and retention which causes hydrocephalus and its associated problem states were highlighted in the previous background section. Shunting is one technique used to address hydrocephalous and excessive CSF. This approach utilizes a catheter to drain Cerebrospinal Fluid (CSF) from the brain, a catheter used to convey the CSF to another region of the vascular, and a valve in between to regulate the flow of CSF between the two catheters. This valve ensures the right amount of CSF is drained from the brain. Too much CSF drainage will cause adverse effects since there will not be enough CSF to perform its natural function—including acting as a cushion for the brain, acting as a mechanism for delivering nutrients from and removing waste from the brain, and regulating changes in pressure within the brain. Too little CSF drainage will still leave the patient dealing with the problem of excessive CSF, including hydrocephalus.

The shunt system can redirect the CSF to various areas of the body including lungs, heart, or other regions of the brain. VP shunting, involving redirection of the CSF to the peritoneal cavity in the abdomen, is one popular shunting technique. Though the shunting systems, devices, techniques, and methods described in the inventive embodiments herein will often be described for us with VP shunts (that is, shunting systems routing CSF to the abdominal section), it can also be used in shunt systems redirecting CSF elsewhere in the body/vasculature.

FIG. 1 shows the broad overview of a VP shunt system 100. The shunt acts to move CSF from the brain 102 to the abdominal peritoneal cavity 110. Here, the shunt system includes a collection or ventricular catheter 104 collecting CSF in the ventricles of the brain and conveying CSF away from the ventricles of brain 102. The system further includes a secondary exit or drainage catheter 108 to direct the collected CSF into the peritoneal cavity 110 of the abdomen. A valve 106 regulating flow between the two catheters is between the two catheters 104, 108. The valve's purpose is to regulate how much CSF is conveyed from the brain (via ventricular catheter 104) to the abdomen (via drainage catheter 108). The valve 106 can include a number of mechanical/electrical valve mechanisms commonly known in the art to regulate the flow.

Shunting has relatively high failure rates, there are an estimated 18,000-33,000 shunts placed each year in the US however up to ⅓ of these fail within the first year and up to 50% fail within the first two years. The causes of failure are numerous, including mechanical failure with the flow valve which drains CSF, and material buildup in the catheters which causes blockages. Often times the CSF has proteins or calcium and these materials can build up in the catheters, leading to clogging of the catheter draining system. This problem is more pronounced in the ventricular catheter which acts as the entry point for the brain CSF to enter the shunt system, and which therefore is exposed to more CSF. Over time, this can lessen how effective shunting is to redirect CSF as the catheter gets filled with more material buildup. Over time this may necessitate the implantation of a new ventricular catheter or an entirely new shunting system.

Figure 2:
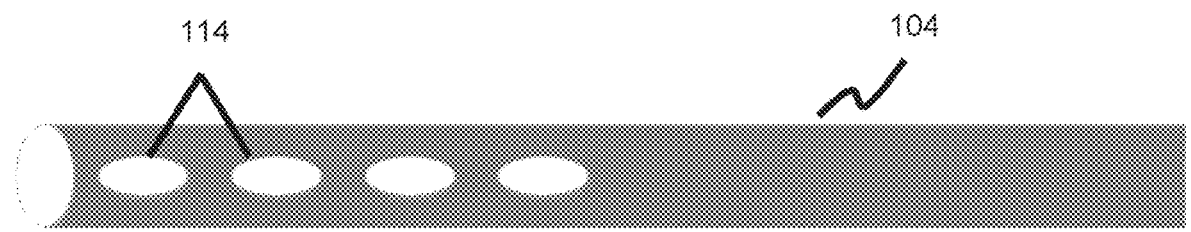
FIG. 2 illustrates a ventricular catheter with a plurality of slits allowing entry of CSF.

The ventricular catheter 104 is shown in more detail in FIG. 2. The ventricular catheter 104 typically includes a number of holes or slits 114 spaced along the end section of the catheter (i.e., the portion of the ventricular catheter 104 which is farthest relative to valve 106, which is the portion of the ventricular catheter 104 which will be exposed to CSF in the ventricles). These holes or slits 114 act as entry conduits for the CSF to enter the ventricular catheter 104. A number of spaced holes/slits are preferred so there are ample points of entry for the CSF to enter the catheter, thereby maximizing the drainage potential. Though four holes/slits 114 are shown in FIG. 2, this is just illustrative and fewer or more holes can be used, including said slits or holes being located along various portions of the ventricular catheter 104. These holes or slits 114 are often where the matter buildup from CSF (e.g., protein or calcium deposits) tends to accumulate. Over time as the material builds up in these entry ports, less and less CSF is able to enter the ventricular catheter—in turn inhibiting the ability of the shunt system to function effectively to drain CSF. The following inventive embodiments presented address this issue by providing various mechanisms used to clean these slits or holes.

Figure 3:
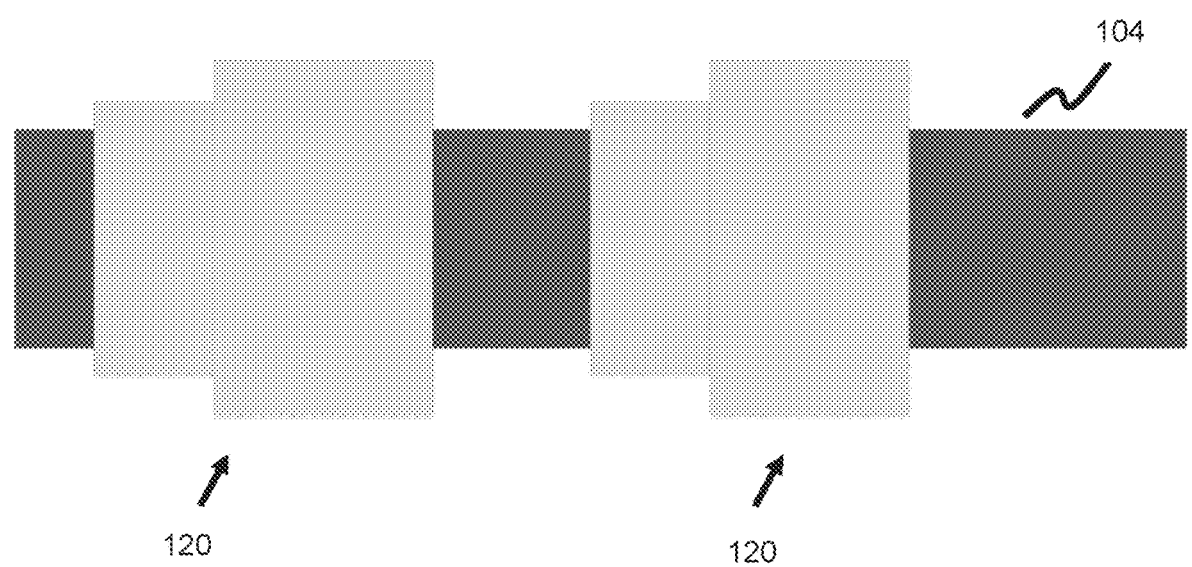
FIG. 3 illustrates a spring-plunger cleaning mechanism in an extended configuration used with a ventricular catheter, according to one embodiment.
Figure 4:
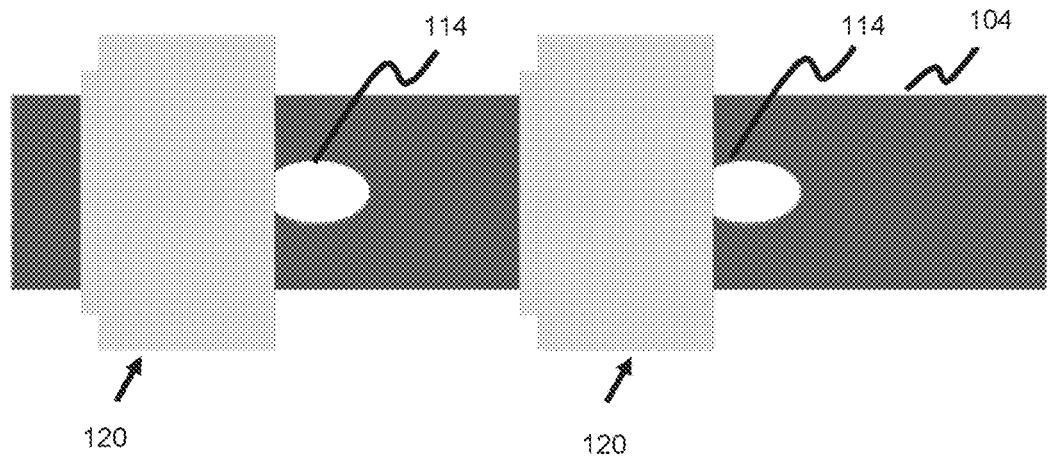
FIG. 4 illustrates a spring-plunger cleaning mechanism in a retracted configuration used with a ventricular catheter, according to one embodiment.

FIGS. 3-4 illustrate one embodiment of a cleaning mechanism 120 used to clean the CSF entry slits 114 of ventricular catheter 104. The mechanism 120 is built over a section of the ventricular catheter 104 and sits over the CSF entry holes 114. Cleaning mechanism 120 utilizes a reciprocating approach to clean the entry slits 114, wherein the mechanism has a first expanded position where it covers the slit and a second contracted position where the slits is exposed. In one embodiment, one mechanism 120 is used for each slit of the ventricular catheter. In one embodiment, each mechanism 120 covers a plurality of slits so that a plurality of slits are cleaned with each cleaning mechanism 120. In one embodiment, cleaning mechanism 120 utilizes a spring plunger as the basis of the reciprocating motion—shown in more detail in FIGS. 5-6. Cleaning mechanism 120 utilizes a spring plunger system which includes a fixed base piece 122 and movable reciprocating piece 132. The fixed base piece 122 has a platform 124, with one or more springs 126 connected to the platform. One end of spring(s) 126 is connected to the platform 124 while the other end of spring(s) 126 is connected to the reciprocating piece 132. The reciprocating piece is hollow in that it is not completely solid—preferably this involves the use of a thin outer wall and a thin inner wall, where the springs are located between these two wall sections. In this manner the spring 126 can connect to the reciprocating piece 132. Base piece 122 and reciprocating piece 126 each include an inner lumen, this lumen is necessary so that the entire cleaning mechanism 120 can slide over the ventricular catheter; therefore, the inner lumen of the base piece 122 and the inner lumen of the reciprocating piece 132 will be larger than the outer diameter of the ventricular catheter 104. These lumens are shown in more detail in FIGS. 7-8, where fixed piece 122 includes an inner lumen 122a which is sized larger than the ventricular catheter outer diameter and movable piece 132 also includes an inner lumen 132a sized larger than the ventricular catheter outer diameter.

Figures 5, 6:
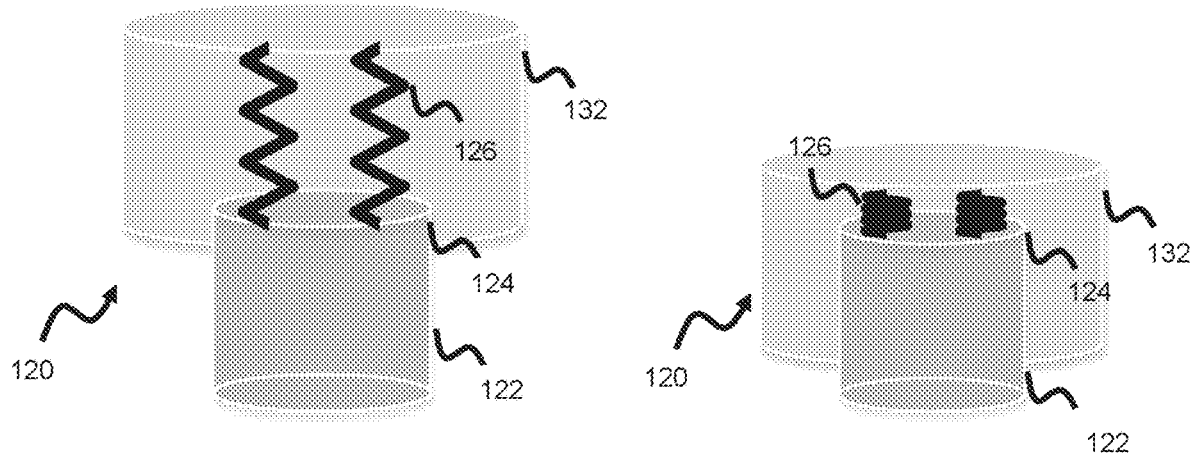
FIG. 5 illustrates a closer view of the spring-plunger cleaning mechanism of FIG. 3 in an extended configuration.
FIG. 6 illustrates a closer view of the spring-plunger cleaning mechanism of FIG. 4 in a retracted configuration.

Though one or more spring(s) 126 are contemplated, in one embodiment, a plurality of springs 126 are used which are spaced in equivalent circumferential intervals along the inner part of the movable piece 132. When springs 126 are fully elongated, the reciprocating piece will be located in its farthest position relative to the base piece, as shown in FIGS. 3 and 5; this corresponds to the reciprocating piece 132 covering an associated slit 114. When the springs 126 are fully compressed, the reciprocating piece will retract relative to the base piece, as shown in FIGS. 4 and 6; this corresponds to the reciprocating piece 132 exposing an associated slit 114 thereby facilitating easier entry of CSF into the associated slit/hole 114.

Figure 7:
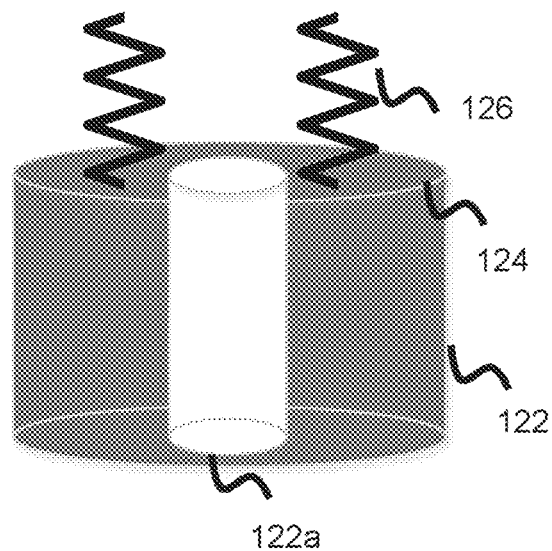
FIG. 7 illustrates a fixed piece of a spring-plunger cleaning mechanism, according to one embodiment.
Figure 8:
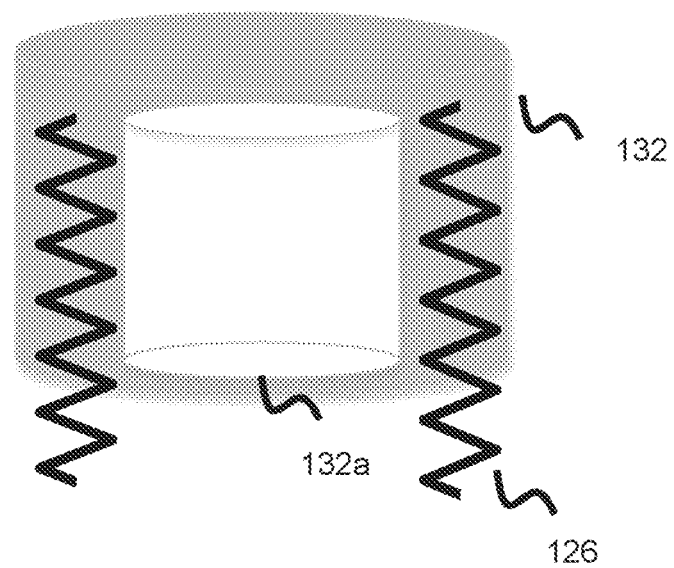
FIG. 8 illustrates a movable piece of a spring-plunger cleaning mechanism, according to one embodiment.

Base piece 122 and moveable piece 132 are shown in more detail in FIGS. 7-8. FIG. 7 shows the base piece 122, which includes the inner lumen 122a which allows the piece to be mounted over the ventricular catheter. Inner lumen 122a should therefore be a larger size than the ventricular catheter so that it can be placed over it, as described above. The fixed/base piece 122 also includes a platform 124 which the one or more springs 126 are attached to, as discussed above.

FIG. 8 shows movable/reciprocating piece 132 in more detail. The movable piece 132 is movable relative to both the ventricular catheter 104 and the fixed piece 122. Movable piece 132 includes its own lumen 132a so that it can be placed over the ventricular catheter and is therefore sized larger than the ventricular catheter, as described above. This lumen 132a is preferably sized larger than fixed piece 132 so that the movable piece 132 can slide over fixed piece 122, in the manner shown in FIGS. 4 and 6 when the springs are compressed. Movable piece 132 is hollow in that there is a first outer wall defining the outer perimeter of the movable piece 132, a second wall defining the inner lumen 132a, and open space in between. The springs 126 span this open space channel section and are attached to the interior of the movable piece 132. The other end of spring(s) 126 is attached to the platform section of fixed base piece 122, as described earlier. While base piece 122 is mechanically fixed to the ventricular catheter surface (e.g., through a connection medium such as adhesive, welds, or other means between the base piece inner lumen 122a and the underlying ventricular catheter), the movable piece 132 is not fixed and in this manner it reciprocates to adopt the positions shown in FIGS. 5-6 as springs 126 contract and elongate. Since the inner lumen 132a of movable piece 132 is larger than the width or diameter of the fixed piece 122, the movable piece 132 overlaps the fixed piece 122 when the spring is collapsed—as shown in FIGS. 4 and 6.

The one or more springs 126 connecting the base piece 122 to reciprocating/moving piece 132 will compress and elongate along with the pressure of the region, which will vary based on blood flow due to the pumping of the heart. Therefore, there should be a relatively consistent cycle of elongation and compression that tracks to the heartbeat and natural flow of blood through the vasculature that results. In this manner, batteries, motors, or other external drivers will not be needed to control the position of movable piece 132, although certain embodiments may utilize these additional elements to electromechanically control the position of movable piece 132.

Figure 9:
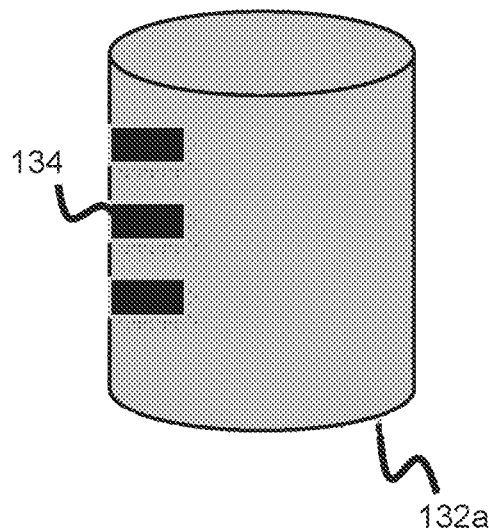
FIG. 9 illustrates an inner lumen of a movable piece of a spring-plunger cleaning mechanism, according to one embodiment.
Figure 10:
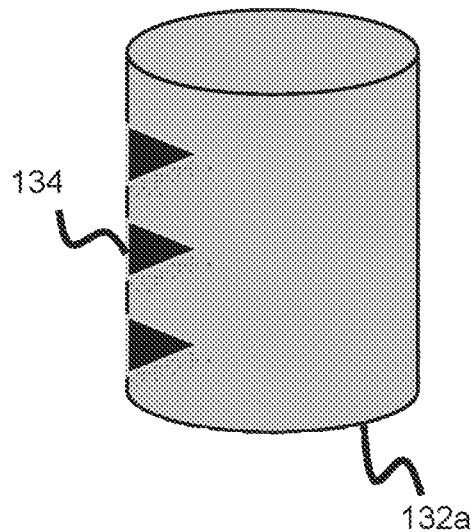
FIG. 10 illustrates an inner lumen of a movable piece of a spring-plunger cleaning mechanism, according to one embodiment.

In terms of the mechanism used to clean the slits 114 as the movable piece 132 passes over them, this can be done in a number of ways. In one embodiment, the wall forming the circumference of inner lumen 132a can include one or more projecting structures that project radially inward within lumen 132a. In this manner, the projecting structures would either graze or physically enter into a portion of the slits 114 as the movable piece 132 passes over the slits, thereby cleaning them. In another embodiment, the wall can include a roughened or abrasive surface which projects slightly into lumen 132a, and which would graze or project slightly into the slits as the movable piece passes over the slits. In another embodiment, one or more brushes are utilized which project from inner lumen 132a. These configurations are shown in FIGS. 9-10 where a projecting element (such as a bar), roughened/abrasive elements, or brush-like elements 134 are shown as extending from within the interior of the inner lumen 134 of the movable piece 132. These cleaning elements 132, 134 could either extend directly from the wall of the inner lumen 132a or could extend from the interior of the movable piece 132 and pass through into the inner lumen 132a.

Since the inner lumen 132a of movable piece 132 is sized larger than the fixed piece 122 (in the manner described earlier, in order to facilitate movement over the fixed piece 122), the projections or roughened surfaces may have to be particularly lengthy in order to contact the holes of the ventricular catheter. One way to mitigate this is to include another smaller internal secondary lumen on movable piece 132, which functions to also fit over the ventricular catheter. Including the smaller secondary lumen will minimize the gap between the ventricular catheter, and including the projections or roughened regions utilized in this smaller secondary lumen will mean the projections/roughened sections can be smaller and still contact the holes or slits to clean them.

In one embodiment, the slits only sit on one side of the catheter, and the inner lumen has projections, abrasions, brushes, or the cleaning surface 134 sitting only along one face of the lumen, as shown in FIGS. 9-10. In another embodiment, the slits are along opposing sides of the catheter. The cleaning surface can then sit along both sides of the lumen to clean the slits on either end. In one embodiment, the cleaning surfaces of the inner lumen 132a of movable piece 132 are radially and/or longitudinally spaced throughout all or a portion of the inner lumen 132a (therefore, located in various areas of the inner lumen 132a).

In one embodiment, a plurality of slits 114 are used along the ventricular catheter 104 and some or all of these slits are configured such that each slit utilizes its own individual cleaning mechanism 120 (as shown in FIG. 4). In one embodiment, a plurality of cleaning mechanisms 120 are used and the movable pieces 132 are connected to each other (e.g. via springs). In this way the motion of some or all of the movable pieces 132 on different cleaning mechanisms 120 can be coordinated together whereby the movable pieces 132 will extend in unison and retract in unison (and not solely relying on the pulsatile nature of blood flow). In those embodiments where an external electromechanical driver is used to drive the movement of movable piece 132, these cycles can be coordinated through a common driver or through a plurality of drivers that are synced together.

Figure 11:
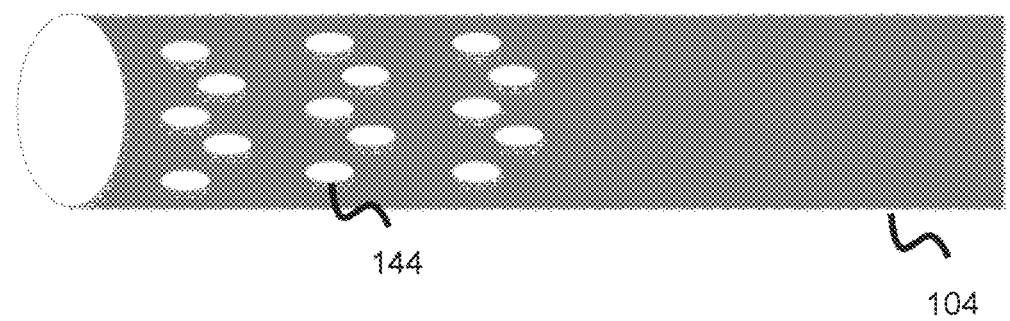
FIG. 11 illustrates a ventricular catheter utilizing a plurality of small CSF entry slits usable with a cleaning mechanism, according to one embodiment.

In one embodiment (shown in FIG. 11), the ventricular catheter 104 may utilize a number of tiny slits 144, rather than utilizing larger slits 114 that are sized so that a single cleaning mechanism can be used for each slit. With this embodiment, a single spring plunger cleaning mechanism 120 as described and shown above in FIGS. 3-10 can be utilized to clean a plurality of these slits. For instance, one cleaning mechanism 120 will span the plurality of slits shown in FIG. 11. The plurality of cleaning surfaces 134 of the inner lumen 132*a* of the movable piece 130 will be used to clean a number of the smaller slits 144. In this manner, one cleaning mechanism 120 can be used to clean a plurality (or all) of the slits 144. In another embodiment, the slits are spaced out over the ventricular catheter in different segments and each segment utilizes its own cleaning mechanism 120 to clean the plurality of slits in that particular catheter segment. The movable pieces can optionally be linked as described above so that the movable pieces move in unison, or otherwise no linking is used and the pulsatile nature of blood controls the movement of the movable pieces (which should generally cause a relatively consistent movement pattern across all the movable pieces).

Figure 12:
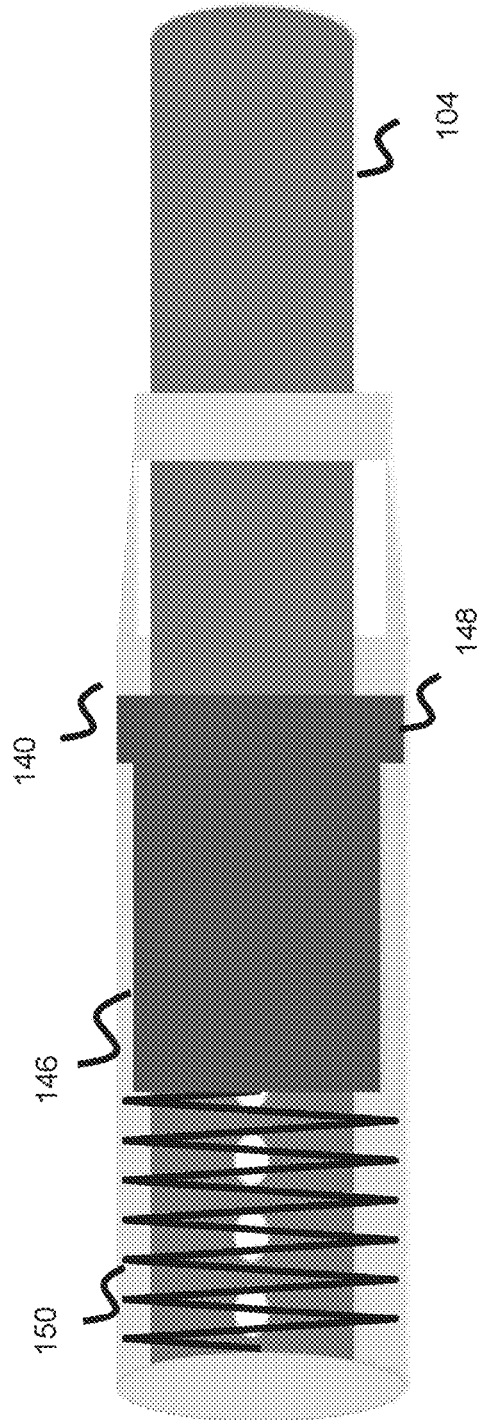
FIG. 12 illustrates a cleaning mechanism utilizing a spring and piston in an extended configuration, according to one embodiment.
Figure 13:
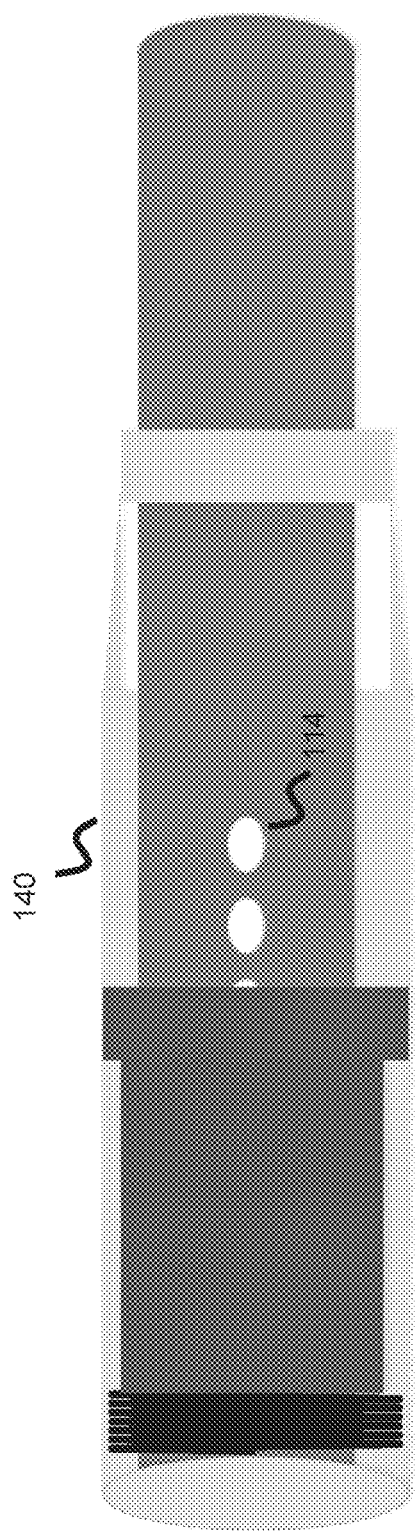
FIG. 13 illustrates a cleaning mechanism utilizing a spring and piston in a contracted configuration, according to one embodiment.

Another embodiment of a cleaning mechanism is shown in FIGS. 12-13. This embodiment utilizes a housing 140 that overlaps an end section of a ventricular catheter 104 (e.g., the section of the ventricular catheter containing CSF entry holes or slits 114). The inside of the housing 140 contains a piston cleaning element 146 with a thickened end region 148, and a spring 150 connected to the piston such that the piston can reciprocate between a proximally oriented configuration and a distally oriented configuration, as shown in FIGS. 12-13. The spring extends and compresses based on various variables. In one example, as CSF collects in the housing, it exerts pressure against the piston 146 and connected spring 150. As this pressure increases, this causes the spring to compress and the attached piston to retract exposing some of the holes 114 of the ventricular catheter and allowing the CSF to then enter the ventricular catheter 104 through these holes 114. In this way, CSF enters the ventricular catheter in a controlled manner depending on how much CSF has accumulated in/near the housing section 140 of the ventricular catheter. The piston has an inner lumen which is sized slightly larger than the ventricular catheter end section, and in this way the piston 146 (as well as housing 140 and spring 150) sit around the ventricular catheter. The inner lumen utilizes the various projections, brushes, or roughened surfaces discussed earlier with regard to the embodiments shown and discussed in FIGS. 3-10 (particularly highlighted in FIGS. 9-10 and associated elements 134). These cleaning elements 134 work in a similar manner to clean the holes 114 as the piston moves back and forth over the holes 114. The thickened end region 148 of the piston slightly contacts the housing and functions to clean the interior surface of the housing from the CSF buildup. This end region 148 can contain a similar projection, brush, or abrasive interface to help clean or scrape the buildup from the interior of the housing 140. This housing element 140 is preferably placed on the very end section of the ventricular catheter where the CSF accumulates in the neurovasculature, in one example this end catheter section would sit within the cerebellopontine angle cistern section of the neurovasculature.

One advantage of the cleaning interface of FIGS. 12-13 is that the CSF drainage is metered since as the CSF accumulates, it exerts pressure on the piston 146 and spring 150. As this pressure increases, it pushes the piston and spring toward the configuration of FIG. 13 exposing more holes 114 as the pressure mounts, thereby increasing the CSF drainage as the pressure increases. Over drainage of CSF is problematic since a certain amount of CSF is needed in the brain to cushion the brain and to help promote proper nutrient absorption. Under-drainage of CSF is bad since this will then cause too much CSF to accumulate leading to increased pressure on the brain and hydrocephalus. In the manner of this embodiment, the CSF drainage is controlled based on the accumulated pressure exerted by the CSF, so some CSF is allowed to accumulate but excess CSF will cause drainage as the pressure builds-up owing to the piston/spring interface. In some examples, the spring tension and piston weight can be customized to precisely control the amount of CSF drainage allowed. In some embodiments, an electrically integrated system is utilized where the spring tension is mechanically customized and altered based on passive measurements taken by an integrated electrical-based measuring system so that the proper drainage is customized based on a measurement system measuring CSF pressure (of the pressure CSF is exerting against the piston 148 and/or spring 150).

In another embodiment similar to the concepts of FIGS. 12-13, a rotating element is connected to a mechanical rod within the housing 140 and this rotating element circulates within the interior of the housing cleaning the holes 114. The rotating element would be located circumferentially around the ventricular catheter 104 between in the space between the catheter and the housing. The rotating element is a disc (with a lumen larger than the ventricular catheter 104 so as to be placed around said catheter) and can utilize various projections or brushes to clean the slits/holes 114. In one embodiment, the disc moves proximally and distally utilizing a connected spring-element, similar to the embodiments of FIGS. 12-13. In another embodiment, one or more discs are used which span a plurality of holes lengthwise along the catheter 104. In another embodiment, no external housing 140 is used—instead, the internal section of the catheter 104 utilizes an end rotating disc element which rotates to clean the various slits 114. In one embodiment, the disc is capable of proximal and distal movement, for instance via connection to an end spring similar to the spring 150 of FIGS. 12-13.

Other embodiments of the present invention can address the issue of CSF and associated matter accumulation along the ventricular catheter fluid entry locations by utilizing particular coatings on the ventricular catheter surface of the section of the ventricular catheter containing CSF entry holes 114. These coatings can either be in addition to the cleaning mechanism concepts discussed above or can be used as a stand-alone solution. For instance, the ventricular catheter or entry holes 114 can be coated with a plasma protein adsorption suppressant, such as, but not limited to, Poly(2-methoxyethylacrylate) (PEMA or X-Coat). Additionally, antibacterial coating can also be used to prevent infection. The entry holes 114 and catheter inner lumen can also be customized to help prevent clogging and obstruction from CSF buildup, for instance larger entry holes and a larger inner lumen can be used to help prevent clogging. Furthermore, the inner wall of the ventricular catheter 104 can also utilize these coatings to prevent material buildup within the catheter itself.

Figure 14:
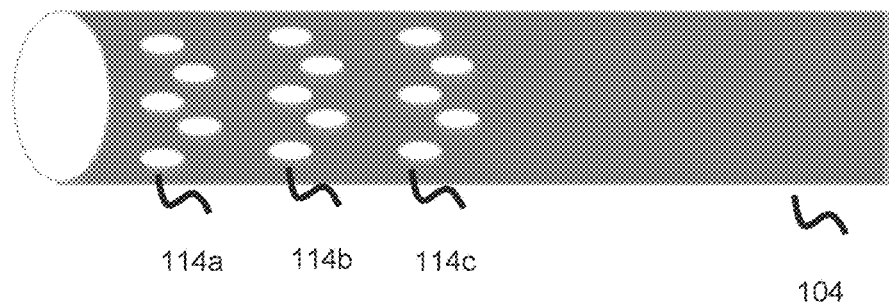
FIG. 14 illustrates a ventricular catheter utilizing a plurality of small slits which can be used with a cleaning mechanism, according to one embodiment.

Other embodiments can utilize a biodegradable or bioresorbable material to cover CSF entry holes 114, whereby the material will degrade or resorb over different time periods to expose the holes. The idea here is that as some holes not utilizing this material get clogged with CSF over time, other holes with degradable or resorbable covering material (which disappears or degrades over time) will then open up allowing CSF to drain through these other holes. The ventricular catheter will be manufactured with extra holes or slits 114. Afterwards, some of the holes will be covered up by a thin film of biodegradable or bioresorbable material such as, but not limited to, polyalpha-hydroxy-acids and/or polyesteramide (PEA), that will take a set amount of time to resorb. Materials with multiple/different resorption rates can be used to cover various holes; this difference in resorption rate can be due to a thicker vs thinner amount of covering material, or alternatively due to different materials being used which have different resorption rates. Additionally, a layer of coating can be applied on the catheter (and/or the flow control valve connected to the ventricular catheter to selectively allow the CSF to drain out of the drainage catheter into the abdomen) to further prevent protein adsorption. FIG. 14 shows an example of a multiple resorption approach, where holes 114*a* are designed as completely open (meaning, without a coating) so these holes will be the initial ones CSF will flow into (but may also clog over time). Holes 114*b* utilize a membrane which resorbs after, for example, 12-24 months—meaning these holes will fully open at 12-24 months which will help account for the portion of holes 114*a* which get clogged. Holes 114*c* can then utilize a membrane covering which resorbs at about 3-4 years, which will help account for the portion of holes 114*a*-114*b* that get clogged. This pattern can continue with various hole segments along the length of the ventricular catheter 104. These holes with different resorption rates can also be spaced in different locations along the catheter to produce a more randomized profile. In this way, as certain holes get clogged, others will open and there is less likelihood of a majority or a plurality of holes all clogging at around the same time (which would undesirably decrease the CSF drainage effectiveness). This approach decreases the chance that a new ventricular catheter will have to be implanted, or at least spaces out the intervals where this procedure will have to be undertaken. One additional advantage of this approach is that a calibrated CSF drainage protocol is maintained. While some holes get clogged over time thereby decreasing their CSF entry/drainage potential, others newly open thereby roughly balancing the total amount of holes/slits available at any given time to evacuate CSF.

The coatings can be applied in various locations, including along the slits/holes/openings 114 of the ventricular catheter, as described. In one embodiment the coating projects outwardly from the holes. In one embodiment the coating is applied such that it projects radially inward from the holes. In one embodiment the coating is flush with the plane of the hole itself. The coating can be applied in a variety of manners including through a mechanical (hand) coating process, or by machine. In one embodiment, the entire catheter (or a portion of the catheter) itself is dipped in the coating solution where the coating is equally applied through the dipped section of the catheter. In some embodiments, the drainage catheter also utilizes the coating in order to prevent bacterial or material buildup. In some embodiments, the coating is utilized along the section of the catheter immediately adjoining the valve so prevent material buildup from interfering with the mechanical valve apparatus.

Aside from ventricular catheter clogging, another complication with the shunting procedure is ensuring the ventricular catheter (which sends CSF from the neurovasculature to the shunt valve apparatus) and the drainage catheter (which routes the CSF from the shunt valve apparatus to the drainage location, such as the abdominal cavity) stay connected to the valve apparatus. If either of these catheters become disconnected or loosened, it limits the ability of the shunt to effectively withdraw and route CSF from the brain. The following embodiments address this issue by providing a locking mechanism to enable a better connection between the shunt valve and the connected catheters.

Figure 15:
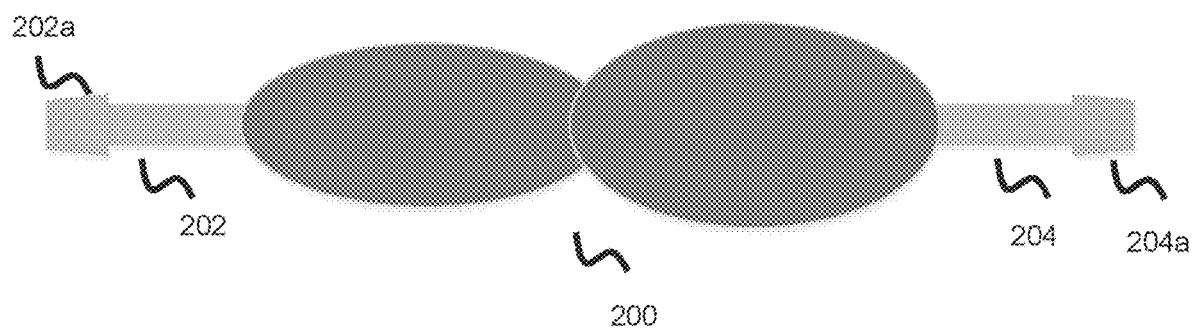
FIG. 15 illustrates a shunt valve interface.

FIG. 15 shows a typical shunt connective interface. The typical system includes a shunt housing/valve 200 which includes a valve element to selectively meter CSF. There is also a first 202 and second 204 connective interface/fitting which connect respectively to a ventricular catheter (a first end of which is in the CSF accumulation region of the brain, and a second end of which is attached to the connective interface 202) and a drainage catheter (a first end of which is attached to the connective interface 204 and a second end of which routes to the drainage region, e.g. the abdomen). The typical interface includes a ridge 202*a* and 204*a* that the catheter is placed over to enable a snug connection between the catheter and the shunt valve. However, this section does not necessarily secure the catheter and the catheter can often become detached from the fitting and the connective interface.

Figure 16:
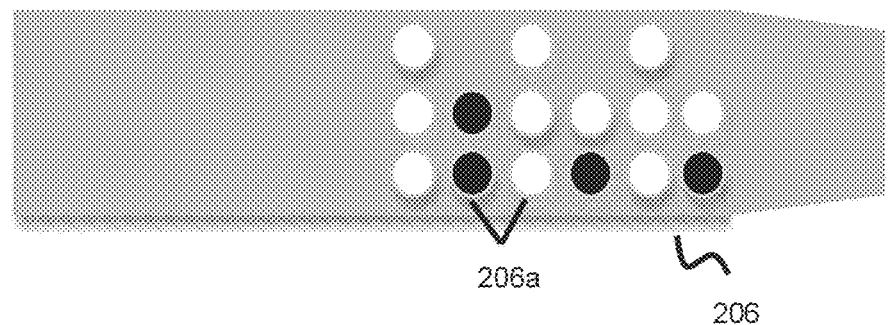
FIG. 16 illustrates a locking mechanism for a shunt valve interface, according to one embodiment.

FIG. 16 shows an embodiment of a connective interface or fitting 206 (this fitting can represent one or either of the two fittings 202, 204 which are at either end of the shunt valve housing 200) utilizing a plurality of connection elements 206*a*. These elements are female depressions or recessions that extend into the surface of the fitting 206, male projections that extend outwardly from the surface of the fitting 206, or some combination of the two. The end section of the catheter—in particular, the section of the catheter that is placed over the fitting—contains a corresponding interface (e.g., a projection that mates with the depression of the fitting 206, a depression that mates with the corresponding projection of the fitting 206, etc.) such that the catheter and fitting are bound by the mating between the respective interfaces. A portion, or all of the connection elements 206*a* can be used whereby the catheter can utilize its own corresponding mating interface that links with a portion or all of the connection elements 206*a*. In one example, the blackened connection elements 206*a* of FIG. 16 can be considered as projections that extend outwardly from the fitting 206, while the whitened connection elements 206*a* can be considered as recesses that inwardly recede from the fitting 206. The corresponding interface surface on the end of the connecting catheter will then have corresponding surfaces to mate with this region (e.g., a recessed or female area to mate with blackened projection 206*a*, and a male projection to mate with whitened female recess 206*a*). Not all of the connection elements 206*a* have to be engaged. For example, a portion of the connection elements 206*a* are actually used to bind the fitting to the overlying catheter. In one embodiment, only projections or only recessed sections are used. For example, the fitting interface 206*a* utilizes only female depressed structures and the catheter interface comprises only male projecting structures—alternatively, the fitting interface 206*a* is only male projection structures and the catheter interface comprises only female recessed structures.

Typical shunt valves utilize a one-way valve design comprising a ruby ball that presses against a spring, where the valve opens up once a certain pressure is reached to allow CSF passage through the valve outlet section and into the drainage catheter. Sometimes, magnets are further used to optimize the desired CSF flow rate for each patient. However, due to the large number of mechanical parts, mechanical failure of valve components is common. The following embodiments discuss a valve concept utilizing fewer mechanical parts to address this valve failure issue.

Figure 17:
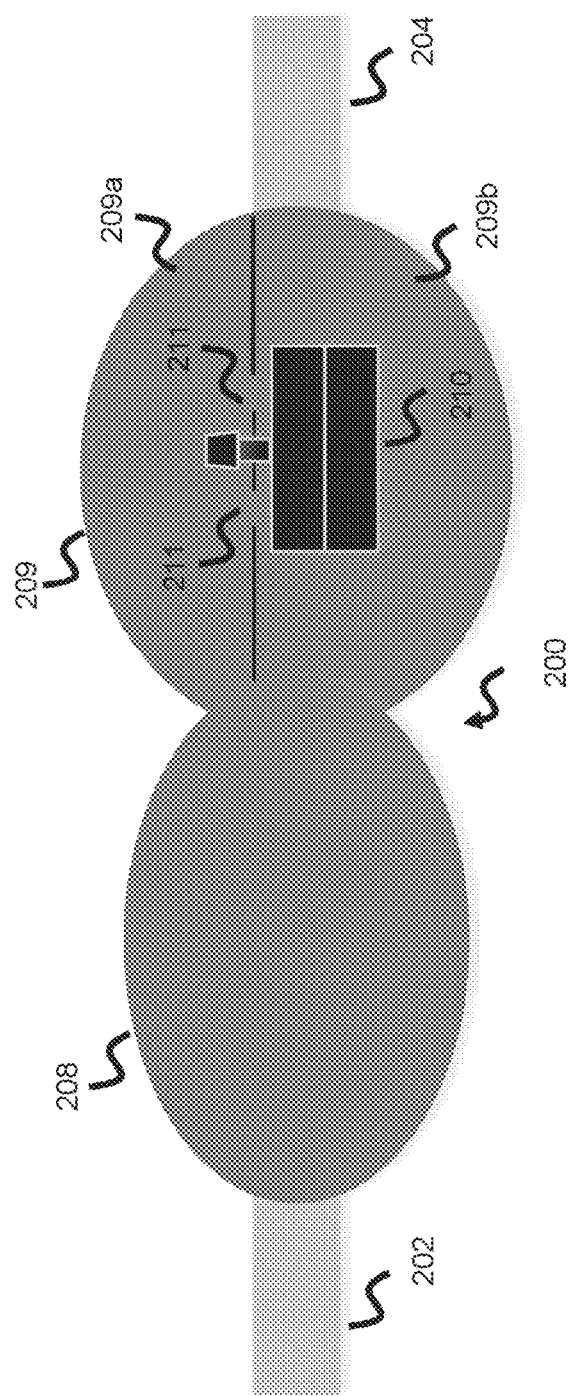
FIG. 17 illustrates a shunt valve system, according to one embodiment.

A shunt valve housing 200 is shown in FIG. 17, including an inlet end 202 connected to a ventricular catheter which collects CSF and an outlet end 204 connected to a drainage catheter which drains CSF. In the context of FIG. 17, CSF will flow left to right. Valve housing 200 includes a pre-chamber 208 and a valve chamber 209 containing a valve 210, where CSF initially follows into the pre-chamber 208 and then into the valve chamber 209. The valve chamber 209 contains a top section 209a and a bottom section 209b, and a valve 210 in between the two sections modulating flow therebetween.

Figure 18:
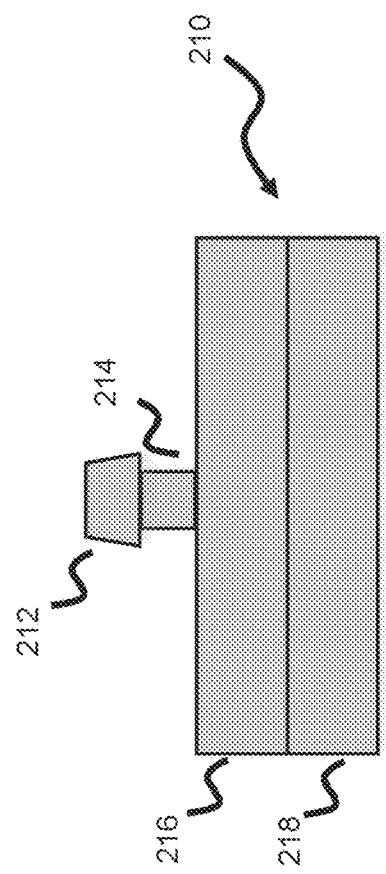
FIG. 18 illustrates the valve used in the shunt valve system of FIG. 17, according to one embodiment.
Figure 19:
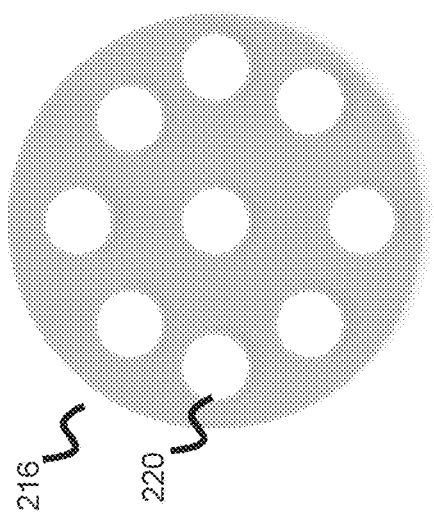
FIG. 19 illustrates a top disc used in a valve, according to one embodiment.
Figure 20:
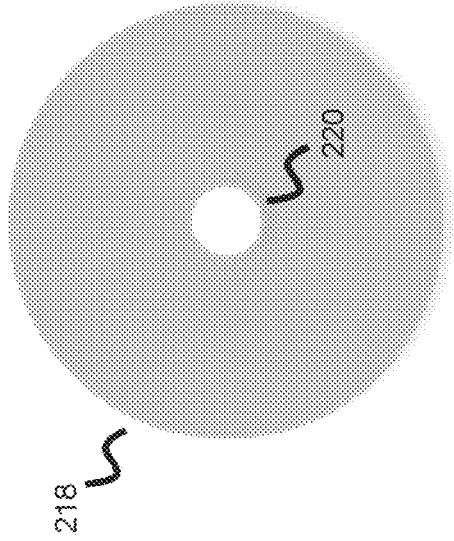
FIG. 20 illustrates a bottom disc used in a valve, according to one embodiment.

Valve 210 is shown in more detail in FIG. 18 and includes a stem 214 and a protruding anchor 212 where the anchor is anchored to the top section of valve chamber 209 through a hole. There are inlet holes 211 around the anchor allowing inflow of CSF as shown in FIG. 17. Valve 210 includes a top disc 216 and a bottom disc 218; both discs are respectively shown in more detail in FIGS. 19-20 and contain a middle hole allowing passage of the valve stem 214 whereby the valve stem 214 binds the two discs together. The mechanical valve operation, which is how the valve 210 opens and closes, will now be explained in more detail.

The valve 210 comprises a top disc 216 and a bottom disc 218, as described above. Top disc 216 contains a number of holes 220 which are aligned with the inlet holes 211 of the valve chamber 209. Once CSF enters the valve chamber 209, it will flow through inlet holes 211 and into the holes 220 of the top disc 216. The bottom disc 218 does not have such a plurality of holes, instead it is weighted such that the a portion of the bottom disc 218 (e.g., the right side of the disc which is the portion which faces the outlet 204) is lighter than the other portion (e.g., the left side). This variable weighting can be accomplished in a number of ways—such as by using lighter material on the lighter portion of the bottom disc 218, or by making a portion of the bottom disc thinner. The CSF weight and pressure increases as it accumulates into the top section of the valve chamber 209 and enters the holes of the top disc 216, the weight will increase whereby the lighter section of the bottom disc 218 will eventually pivot allowing the CSF to exit. This pivoting action means that the stem section 214 is either slightly longer than the bottom disc or is not fixed directly to the bottom disc 218, meaning the bottom disc 218 has some give and has some slight degree of movement as the CSF weight increases.

If enough CSF accumulates, the heavier or thicker left side of the bottom disc will also pivot allowing CSF to now exit through the bottom chamber of the valve chamber 209. In this manner, the valve 210 has a closed configuration when the CSF threshold weight is not surpassed where the top and bottom discs are snug so that CSF cannot exit the valve. The valve 210 next has a partially open configured where the thinner or lighter portion of the bottom disc 218 (e.g., the section of the disc which is closer to the outlet end 204 of the shunt valve system) opens to allow partial CSF outflow. Finally, the valve 210 has a fully opened configuration where the entire bottom disc 208 opens or pivots with respect to the top disc allowing maximum drainage of CSF.

In one embodiment, the valve's 210 discs 216, 218 are both silicone and approximately 0.3 inches in diameter. The top disc 216 is about 0.07" thick and contains 6-8 holes 220 around the perimeter. Bottom disc 218 decreases in thickness as it moves around the disc circumference, as discussed above, where the thickest section is about 0.07" and the thinnest section is about 0.02". Though the earlier description specifically discussed the portion of the bottom disc 218 facing the outlet 204 as the thinnest, in practicality it would not necessarily matter which section of bottom disc 218 is thinner since the CSF will likely accumulate in the bottom chamber 209b of the valve chamber 209 and then be pushed through the outlet 204 once the bottom chamber fills with CSF. Therefore, as long as any portion of the bottom disc 219 is thinner (or lighter), it will allow CSF to drain from the upper section of the valve chamber 209 once a threshold weight or pressure is reached. This design will therefore create a pressure gradient one-way valve, where the two-disc interface prevents CSF from flowing backwards.

The purpose of pre-chamber 208 is to accumulate CSF prior to it entering the valve chamber 209. However, in some embodiments, the pre-chamber 208 can also be used for hypodermic sampling of CSF, and/or can used to test for proper valve function. The pre-chamber can be pressed down or palpated/palpitated for testing purposes. For instance, the valve flow can be configured so a certain amount of fluid always stays in the pre-chamber while not enough fluid stays in the pre-chamber so as to completely fill it. If the pre-chamber bubble cannot be pressed down, it will indicate distal catheter obstruction since the pre-chamber will be completely filled. Meanwhile, if the pre-chamber bubble stays down after being pressurized, it would indicate proximal catheter obstruction—therefore the pre-chamber material characteristics can be configured to act as an indicator of proper functionality of the ventricular (brain) catheter and the drainage (abdominal) catheter.

Often times with the shunt procedure or to otherwise remove excess CSF, a hole is created in the third ventricular area of the neurovasculature to remove excess CSF and reduce pressure on the brain. Often times this procedure is used instead of the shunt procedure or in concert with the shunt procedure to provide a drainage path for CSF back within the bloodstream. However, sealing this opening can be difficult. Hydrogels are a class of compounds that expand or swell in response on a particular stimulus. Hydrogels for vascular therapeutic purposes are often designed to expand based on contact with aqueous material (e.g., the aqueous portion of blood) or based on pH (e.g., the pH of blood). In one embodiment, hydrogels such as but not limited to polyethylene glycol or polytetramethylene oxide can be applied to the area to help seal the created opening. In one embodiment, a portion of the distal tip of the ventricular catheter (meaning the end portion of the ventricular catheter within the neurovasculature CSF accumulation point) utilizes hydrogel, such as the portion that is about 5 centimeters away from the distal tip, to help seal the opening. Alternatively, the hydrogel can be applied using a syringe after the catheter is placed in position within the ventricles of the neurovasculature. Similarly, if a shunt valve is placed endovascularly, a vein such as the inferior petrosal sinus may be punctured to place the valve. The hydrogel can be applied to the tip of the shunt where the shunt is anchored into the vessel wall to seal the puncture and to help keep the shunt firmly in place.

Many of the embodiments presented herein have addressed the problem associated with the clogging of the ventricular catheter or valve failure, where various mechanically-oriented devices and systems were described to address this issue. This problem can also be solved through an electrical communication system utilizing wireless communication protocols to monitor convey changes in intracranial pressure whereby any blockages or other issues with the CSF draining procedure would result in a noticeable increase in intracranial pressure (ICP). ICP is measured over a given time interval and maximum and minimum pressure are stored and analyzed to provide a meaningful representation of ICP, whereby significant deviations would indicate an issue with the shunt system. The information is then transmitted wirelessly through communication protocols such as, but not limited to, Bluetooth Low Energy (BLE) to provide advanced warning of changes in ICP to alert the patient. This information is then wirelessly transferred to portable wireless enabled devices such as watches, mobile phones, mobile computers, etc. The steps and elements required for this system is represented in the flowchart of FIG. 21.

Figure 21:
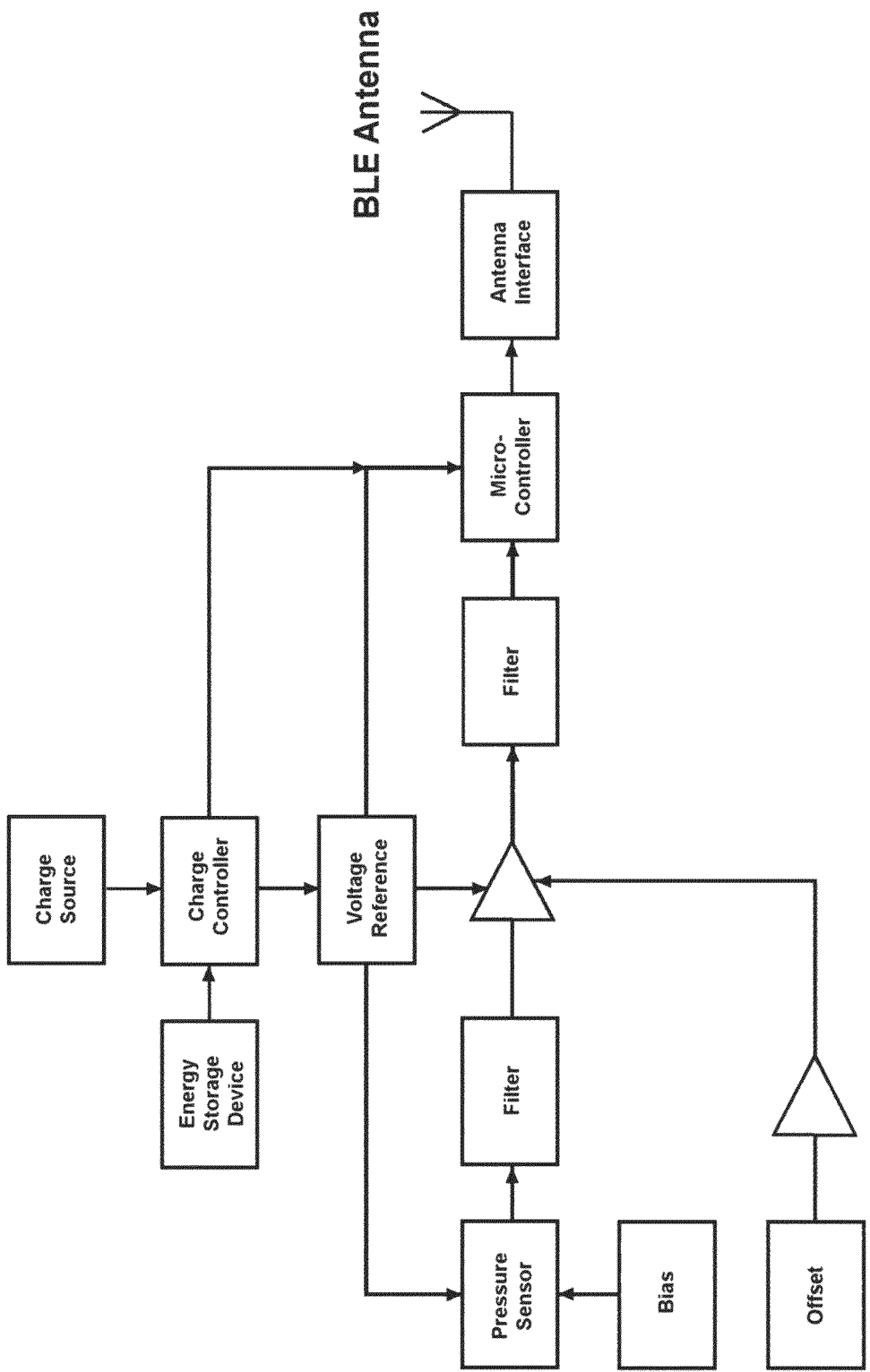
FIG. 21 illustrates a flowchart for an electrical communication system used as part of a shunt system, according to one embodiment.

The pressure sensor which is included in the flowchart of FIG. 21 is used to monitor ICP and in one embodiment uses a micro-electromechanical (MEMS) silicon-based pressure sensor. The silicon-based pressure sensor utilizes the proportional change of resistance elements located within the sensor. The pressure sensor could be placed anywhere within the shunt system, including within the ventricular catheter, valve housing, or drainage catheter—additionally various pressure sensing elements could be placed in different areas of the shunt system (e.g., one in the ventricular catheter and one in the valve housing) to create a broader ICP representation as well as help identify where any blockage is located. Alternatively, a separate pressure sensor can be implanted near the ventricular catheter so that the pressure represents the ICP physically within the ventricular region where the CSF accumulates.

The flowchart also includes an antenna system used to convey data to a wireless enabled device (e.g., a watch, smartphone, computer, or tablet). One embodiment for the antenna portion of the electrical system utilizes a non-magnetic conductive trace pattern (e.g., utilizing gold-plated copper, platinum, beryllium) which is designed into the surface of the shunt catheter and connected to the antenna interface circuitry. The conductive section links a measurement taking sensor (such as the pressure sensor) to the antenna to transmit the relevant data or links the controller which compiles the relevant data to the antenna for transmittal. The conductive pattern is designed to have optical radio frequency transmission characteristics over the selected wireless communication protocol (for instance, BLE frequencies of 2.4-2.4835 GHz).

Another embodiment for the antenna portion of the electrical system utilizes a ventricular anchor. The ventricular anchor exits the CSF accumulation vein of the neurovasculature, and the catheter then is located within the vein, whereby the anchor serves to keep the ventricular catheter in place. This embodiment utilizes a ventricular anchor comprised of conductive material (e.g., stainless steel, platinum cobalt chromium, etc.) with geometry sized for the RF transmission characteristics of the frequencies required, where the anchor itself acts as the antenna or acts as the conductive electrical communication medium for the antenna.

The power requirements for the electrical system is relatively low, requiring approximately 3-4 microwatt-hours each time the ICP is measured and the relevant data transmitted. One embodiment utilizes an energy storage concept to utilizing a capacitive storage element embedded within the walls of the ventricular catheter. The capacitive storage element is constructed of two concentric tubes of different diameters, and the space between the two conductive tubes is filled with a dielectric material. The dielectric has a sufficient dielectric constant to provide large enough capacitance between the two tubes to store sufficient energy for the electrical system to operate. The capacitor is charged through an external charge source such as an inductively coupled charging station or energy harvesting (e.g., thermal, RF or piezo-electrical energy) controlled by the charge controller. Alternatively, the electrical system utilizes a hermetically sealed implantable battery utilizing a lithium-iodine or lithium-carbon fluoride battery.

In one embodiment, the electrical communications system described above and shown in FIG. 21 passively measures ICP to convey this information to an external device to relay this information to the user. In another embodiment, the electrical system varies the valve characteristics (e.g. loosens or tightens the valve to either augment CSF discharge or reduce CSF discharge) based on measured ICP data. As discussed above, a certain amount of CSF is needed so the shunt valve cannot constantly drain CSF but instead typically drains CSF once a certain pressure is exceeded. Typically, this system utilizes a mechanical valve which mechanically opens or mechanically enables flow once a threshold pressure is exceeded. In certain circumstances it can be difficult to design an optimum valve since every patient is different (for instance, each patient will have different brain sizes, different CSF production amounts, etc.). However, with the electrical system described above, the monitoring system itself can link to the valve and open or close the valve based on the calculated ICP to provide a customizable valve profile. In this way, once a certain threshold value is exceeded, the electrical system communicates with the valve and then opens the electro-mechanical valve. This threshold value can constantly be updated based on observed phenomena or can be calibrated based on a stored physician-enabled profile. This system can also be used to continuously monitor CSF and make continuous small adjustments valve to control how "open" the valve is to create a constantly updated valve profile where small adjustments in the valve opening profile are being made on a relatively continuous basis as needed. In this way, a master electrical communication system is used to monitor ICP. This system is then directly linked to the valve to adjust the valve to enable more CSF flow through the valve or limit CSF flow through the valve, as needed.

One issue with shunts is how the CSF drainage rate changes when a person goes from a supine or flat position (e.g. when sleeping) to an upright position. Due to gravity, this movement change can cause CSF to suddenly drain since the drainage catheter goes from a horizontal position to a vertical position as the patient sits upright. However, this increase in drainage can be undesirable since it is in response to a change in patient orientation, rather than resulting from an accumulation of CSF. CSF over drainage is risky because too little CSF in the neurovasculature can cause ventricles to collapse, tearing of blood vessels, headaches, subdural hematoma, slit ventricle syndrome where the ventricles decrease in size, too little brain cushion, and/or reduce the nutrient absorption and waste removal process. One embodiment of the present invention addresses this issue by utilizing an electromechanical valve which adjusts and regulates the flow of the valve with the use of sensors measuring CSF pressure and flow. One or more micro-accelerometer sensors are integrated into the shunt valve or placed along the catheter tubing, these sensors are used to detect the movement and orientation (e.g., supine or upright) of the patient. Once the shunt is implanted, the physician calibrates the micro-accelerometers by creating baseline orientations of the patient at different body positions. Once calibrated, the accelerometers determine whether the patient is supine, upright, partially supine, partially upright, etc. When the accelerometers determine the patient is moving from a supine/horizontal position to an upright position, a signal is sent to the electromechanical valve to reduce the flow to prevent over drainage of CSF. Small changes can also be made as small changes are observed (e.g. as a patient goes from a sitting position to a standing position, or a slouched position to a straightened position). In addition to pre-programmed flow adjustment based on body positions, the CSF shunt could also be programmed with an AI algorithm whereby a downstream flow sensor (e.g., one in the drainage catheter) is used to detect the effectiveness of the last occurrence the valve was adjusted to prevent over-siphoning/over-drainage of CSF. The settings of the valve based on various body positions are stored in the memory of the device, where after each occurrence the program uses stored historical data to pinpoint the best settings to prevent siphoning based on body position changes, and the corresponding flow characteristics of the electromechanical shunt valve. In this manner, the patient would have the most optimal settings for anti-siphoning and require less visits to the physician for valve adjustments. The system can also be used with the wireless system described above and shown in FIG. 21 to communicate and monitor ICP characteristics, where the position of the user is another measurement the system is configured to monitor and adjust based on observed phenomena.

What is claimed is:

1. An implantable fluid shunt comprising:
a catheter;
a plurality of openings along a portion of the catheter facilitating entry of a bodily fluid into the catheter;
a cleaning mechanism connected to the catheter and movable over the plurality of openings between a proximal position and a distal position; wherein the cleaning mechanism is biased towards either the proximal position or the distal position with bias force that allows movement of the cleaning mechanism between the proximal position and the distal position from forces placed on the cleaning mechanism by the bodily fluid.

2. The implantable fluid shunt of claim 1, further comprising wherein the cleaning mechanism includes a projection adapted to contact a portion of one or more of the plurality of slits.

3. The implantable fluid shunt of claim 2, wherein the cleaning mechanism includes an inner lumen and the projection projects from the inner lumen.

4. The implantable fluid shunt of claim 1, wherein the cleaning mechanism includes an inner lumen which is larger than an outer diameter of the catheter.

5. A cerebrospinal fluid shunt comprising:
a ventricular catheter;
a plurality of slits along a portion of the ventricular catheter facilitating entry of cerebrospinal fluid into the ventricular catheter;
a housing positioned over a portion of the ventricular catheter;
a cleaning mechanism positioned between the housing and the ventricular catheter, the cleaning mechanism having a movable element which moves relative to the ventricular catheter;
wherein the movable element is adapted to clean one or more of the plurality of slits of the ventricular catheter as the cleaning mechanism moves relative to the ventricular catheter;
wherein the movable element comprises a piston connected to the housing with a spring, thereby allowing the piston to reciprocate in response to forces placed on the piston by the cerebrospinal fluid.

6. The cerebrospinal fluid shunt of claim 5, wherein the piston includes an internal projection adapted to contact one or more of the plurality of slits.

7. The cerebrospinal fluid shunt of claim 5, wherein the piston includes an external projection adapted to contact the housing.

8. An implantable fluid shunt comprising:
a catheter;
a plurality of openings along a portion of the catheter;
a housing positioned over a portion of the catheter;
a piston positioned between the housing and the catheter, the piston being movable over the plurality of openings between an unbiased position and a biased position; and
wherein the piston is connected to at least one of the housing or the catheter, such that in the biased position the piston is biased to move over one or more of the plurality of openings and towards the unbiased position.

9. The implantable fluid shunt of claim 1, wherein the catheter is an intravascular catheter and the bodily fluid is a cerebrospinal fluid.

10. The implantable fluid shunt of claim 1, further comprising an electromechanical driver for driving movement of the cleaning mechanism.

11. The implantable fluid shunt of claim 1, wherein the cleaning mechanism includes a spring plunger.

12. The implantable fluid shunt of claim 1, wherein the cleaning mechanism includes a plurality of movable pieces, the movable pieces being linked such that the movable pieces move in unison.

13. The implantable fluid shunt of claim 1, wherein the cleaning mechanism retracts in response to an increase in the forces placed on the cleaning mechanism by the bodily fluid.

14. The implantable fluid shunt of claim 1, wherein the cleaning mechanism includes a rotating element.

15. The implantable fluid shunt of claim 14, wherein the rotating element includes a disc.

16. The implantable fluid shunt of claim 1, wherein the cleaning mechanism includes one or more brushes or one or more abrasive surfaces.

17. The implantable fluid shunt of claim 1, further comprising a drainage catheter and a shunt valve selectively metering the bodily fluid, wherein the shunt valve is connected at a first end to the catheter and at a second end to the drainage catheter.

18. The implantable fluid shunt of claim 17, wherein the shunt valve includes a plurality of discs.

19. The implantable fluid shunt of claim 18, wherein the plurality of discs comprises an upper disc and a lower disc.

20. The implantable fluid shunt of claim 1, further comprising a position sensor detecting movement and orientation of a patient in whom the implantable fluid shunt is implanted.

* * * * *